United States Patent [19] [11] Patent Number: 5,398,019
Barnett et al. [45] Date of Patent: Mar. 14, 1995

[54] PORTABLE SENSOR FOR DETECTING BENDS OF THE BACK OF A PERSON PAST A PREDETERMINED LUMBOSACRAL ANGLE

[75] Inventors: Larry W. Barnett, 29 Weatherbell Dr., Norwalk, Conn. 06851; John E. Pfeifer, Redding, Conn.

[73] Assignee: Larry W. Barnett, Norwalk, Conn.

[21] Appl. No.: 171,849

[22] Filed: Dec. 22, 1993

Related U.S. Application Data

[63] Continuation of Ser. No. 748,275, Aug. 21, 1991, abandoned, which is a continuation-in-part of Ser. No. 640,699, Jan. 14, 1991, abandoned.

[51] Int. Cl.⁶ .............................................. G08B 21/00
[52] U.S. Cl. .................................... 340/689; 340/573; 200/61.52; 200/DIG. 2
[58] Field of Search ............... 340/686, 689, 571, 573, 340/693, 575, 323 R; 200/61.52, DIG. 2, 61.45 R; 128/781, 782

[56] References Cited

U.S. PATENT DOCUMENTS

| | | | |
|---|---|---|---|
| 3,362,023 | 1/1968 | McMahon | 340/689 |
| 3,728,675 | 4/1973 | Horn et al. | 340/539 |
| 4,007,733 | 2/1977 | Celeste | 128/781 |
| 4,353,375 | 10/1982 | Colburn | 128/782 |
| 4,536,755 | 8/1985 | Holzgang | 340/689 |
| 4,665,388 | 5/1987 | Ivie et al. | 340/573 |
| 4,938,476 | 7/1990 | Brunelle et al. | 340/573 |
| 4,958,145 | 9/1990 | Morris | 340/689 |
| 4,972,177 | 11/1990 | Nolan | 200/DIG. 2 |
| 5,038,137 | 8/1991 | Lloyd | 340/689 |
| 5,089,808 | 2/1992 | Amirdash | 340/689 |
| 5,128,655 | 7/1992 | Shore | 340/572 |
| 5,168,264 | 12/1992 | Agustin | 340/573 |

FOREIGN PATENT DOCUMENTS

| | | | |
|---|---|---|---|
| 2045492 | 10/1980 | United Kingdom | 340/573 |
| 1595788 | 8/1981 | United Kingdom | 340/573 |
| 8303747 | 11/1983 | WIPO | 340/573 |

*Primary Examiner*—Hezron E. Williams
*Assistant Examiner*—Christine K. Oda
*Attorney, Agent, or Firm*—St. Onge Steward Johnston & Reens

[57] ABSTRACT

A torso attitude sensor for attachment to a human A torso at the waist. It senses when a human torso bends past a predetermined lumbosacral angle and sounds an alarm. The sensor may be worn on the left or right side of the waist because it includes two attitude responsive switches which are inclined in directions opposite to each other. The device further includes a counter for determining the number of times the electrical circuit is connected thereby providing the person, or his or her manager, with an indication of the number of times improper bending occurs. A timer is included with which actuation of an attitude responsive switch must persist for a minimum time interval before an alarm signal or excessive bending signal is generated.

1 Claim, 6 Drawing Sheets

PORTABLE SENSOR FOR DETECTING BENDS OF THE BACK OF A PERSON PAST A PREDETERMINED LUMBOSACRAL ANGLE

This is a continuation of copending application Ser. No. 07/748,275, filed on Aug. 21, 1991, now abandoned, which is a continuation-in-part of patent application Ser. No. 07/640,699, filed Jan. 14, 1991, abandoned.

BACKGROUND OF THE INVENTION

1. Field of the Invention

The present invention relates to a device which is attached at the waist of a human torso, and which senses improper bending and sounds an audible alarm. More particularly, in industrial and other settings, when a person bends to lift a weight or perform some other activity, it is recommended for medical purposes that the person bend his or her knees and attempt to keep his or her spine upright. Most experts agree that improper bending occurs when a person bends at the waist to lift weight or performs some other activity. During bending, it is recommended that the bend at the waist does not exceed a predetermined lumbosacral angle. When a person bends the spine past this angle, most experts consider this improper bending that should be discouraged.

Devices that sense and respond to bending of the human body are disclosed in U.S. Pat. No. 4,938,476 to Brunelle et al., U.S. Pat. No. 4,665,388 to Ivie et al. and U.S. Pat. No. 4,958,145 to Morris. The Brunelle et al. patent discloses a device including a circuit having a mercury switch and an alarm for determining when the body bends beyond a predetermined lumbosacral angle. The Ivie et al. patent discloses a similar device. However, these devices have several drawbacks. Firstly, when an indicator is used in industry by a large number of people, it is often difficult to assure proper use of the device when it is meant for single side placement as shown in FIGS. 1 and 3 of the Brunelle patent. In practice, some people may find it more comfortable to wear the device on the right side, or it may be simply difficult to assure proper use because a person may switch the device to the non-sensing side. In addition, these prior art devices require a specific and complicated mechanism for attaching the back-angle-sensing devices.

These patents disclose the use of a buzzer to indicate to the person wearing the device that he has bent improperly. However, in industry settings, it is important for management to monitor how well a particular person follows recommended lifting technique over an extended period of time.

In addition, these patents disclose use of mercury switches that will sound an alarm each time the switch closes even in response to a simple jarring motion. For example, if a person moves abruptly, the mercury switch, or such other switch for sensing attitude, may connect the circuit and set off the buzzer. In almost any setting, it is annoying to have the buzzer sound when improper bending is not likely to occur or has not occurred.

It is, therefore, an object of the invention to provide a torso attitude sensor that can be worn on the left or the right side of a human torso and indicate improper bending regardless of which side the sensor is attached to. It is a further object of the invention to provide a device which will monitor personnel bending activity over an extended length of time, so that the person or management in a factory setting can determine whether or not recommended lifting techniques are being followed. It is a further object of the invention to prevent or minimize the number of false alarms in a back-bending sensing device.

SUMMARY OF THE INVENTION

These objects are achieved in one embodiment in accordance with the invention by employing a torso attitude sensor that is convenient to apply and wear and can be used on either side of the waist. This is achieved in one form of the invention by using a pair of attitude sensitive switches that are so aligned that whether or not the wearer uses the device on the left or the right side, an alarm is set off when the wearer bends to the critical lumbosacral angle. The attitude-sensing switches are mounted on a common printed circuit board and so electrically connected that the bending activation of either one for at least a minimum interval results in an alarm.

The electrical circuit to which the back-attitude-sensing switches are coupled is desensitized so that inadvertent or abrupt motions by the wearer does not set off the alarm. This is achieved by requiring that an attitude-sensing switch remains activated for at least some minimum interval before a bend alarm arises.

With a torso attitude-sensing device of this invention, the device can remain continuously ready for use without an on/off switch, yet without power drain of a battery. This permits continuous monitoring of a person's bending activity. During rest or other non-use times, the device normally rests in an inclined position in which neither attitude-sensing switch is activated.

In accordance with one aspect of the present invention, the torso attitude sensor can be attached to either the left or right side of a person's waist and operate to send an alarm when the person bends past the predetermined lumbosacral angle. In a factory setting, people need not have to understand precisely how the sensor is to be used, and may choose to place the sensor on either the left or right side of their waist. Thus, it is a significant improvement that this back-bending sensor can be placed on either side of the waist and still perform the function.

The sensor comprises a support for attachment to the waist at a lateral position. At least two attitude responsive switches, preferably, mercury switches, are secured with respect to the support. One attitude responsive switch is actuated when the housing is inclined by a predetermined angle. The second attitude responsive switch is actuated when the housing is inclined by said predetermined angle in an opposite direction. A person can bend forward improperly to actuate one of the attitude responsive switches. However, it would be impossible biomechanically, for the same person to bend backwards sufficiently far to operate the other attitude responsive switch. Therefore, independent of which side the sensor is placed, the torso attitude sensor actuates properly. The device also includes an audible signal such as a buzzer that goes off when one of the switches is actuated.

In accordance with another aspect of the invention, a counter is provided for determining the number of times an attitude-sensing switch has been actuated, and includes a display for showing the number of times the switch has been actuated. Reset of the counter is provided but access to this by the user preferably is made difficult when the performance of persons using the device is to be monitored.

In accordance with another aspect of the invention, the circuitry may include means such as a delay for preventing the signal from an attitude-sensing switch to actuate the counter unless the attitude-sensing switch has been actuated for a predetermined length of time. This prevents the counter from being actuated when a person moves suddenly while wearing the switch, but does not bend beyond a predetermined lumbosacral angle.

In accordance with still another aspect of the invention, the mercury switches each have a longitudinal axis and the axis of both of the mercury switches is inclined with respect to the vertical by a predetermined angle. Both of the axis of the switches are located in the same plane and are inclined in opposite directions with respect to a vertical axis. In accordance with another aspect of the invention, the attitude responsive switches are adjustable internally to set the angle at various degrees with respect to vertical.

Further advantages and features will be described with respect to the below detailed description of the invention with respect to the drawings.

DETAILED DESCRIPTION OF THE INVENTION

Figure 1:
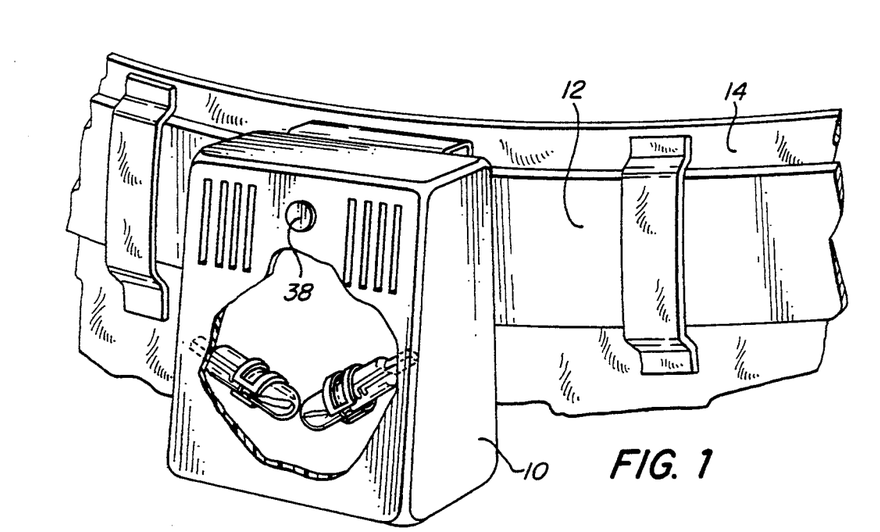
FIG. 1 is a perspective view of a torso attitude sensor attached at the waist of a human torso.
Figure 2:
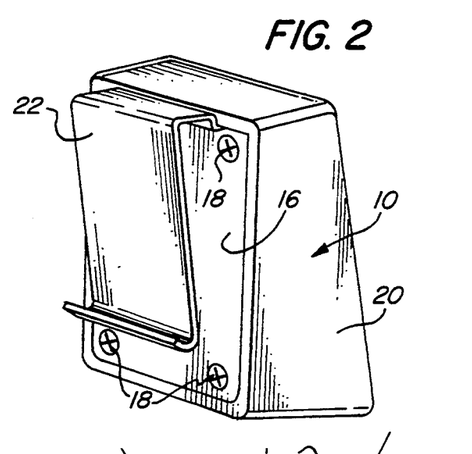
FIG. 2 is a perspective view of the back of the torso attitude sensor shown in FIG. 1.

Referring to FIGS. 1 and 2, a torso attitude sensor 10 in accordance with the present invention is shown. Also shown in FIG. 1 is a belt 12 that is attached to pants 14, which are worn by a human torso. The sensor 10 is attached to the belt at the lateral side of a human waist. As shown in FIGS. 1 and 2, the sensor includes a support 16 that is attached by a series of screws 18 to a cover 20. Although various means of attachment to a human torso can be provided, the sensor of the present invention includes a belt clip 22 which is secured with respect to support 16. The belt clip as shown in FIG. 1 attaches the sensor to the human torso in a vertical position. Preferably, the base of the cover is flat so that when the sensor is not in use, it can be stored in an upright position.

Figure 3:
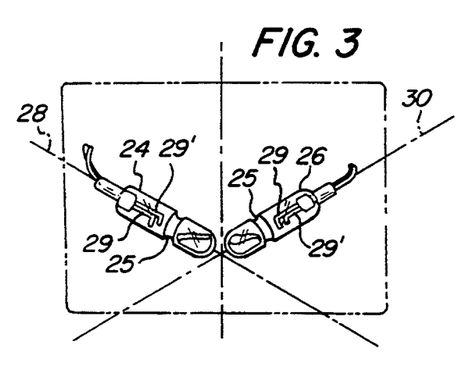
FIG. 3 is a schematic view of the two mercury switches shown in a rest position.
Figure 4:
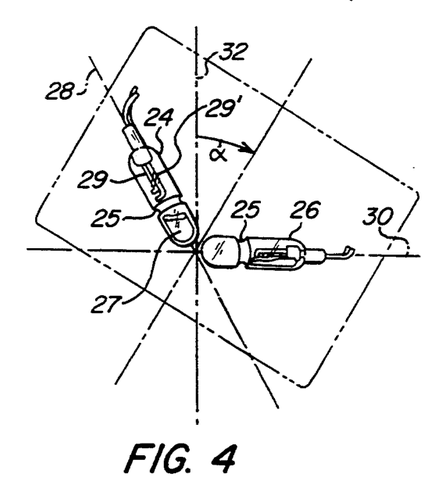
FIG. 4 is a schematic view of the mercury switches wherein the attitude sensor has been tilted by an angle with respect to vertical.
Figure 5:
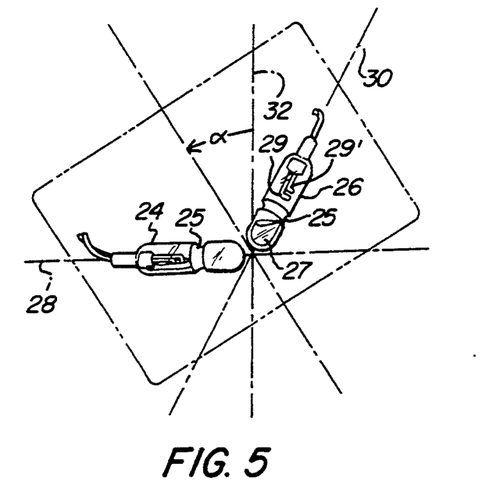
FIG. 5 is a schematic view similar to FIG. 4 except that the torso attitude sensor has been tilted in an opposite direction.

Referring to FIGS. 3–5, the torso attitude sensor in accordance with the present invention, includes two attitude responsive switches 24 and 26 which are preferably mercury switches. However, other types of attitude-sensing switches may be used including a ball type and an accelerometer type. The mercury switches are preferably of the type with a ridge 25 that extends around the interior sidewall of each switch. The ridge 25 stops the flow of mercury until the switch has been pivoted past a predetermined angle and reduces or prevents false reading by the mercury bouncing into the contacts when the sensor is momentarily jarred.

The mercury switches 24 and 26 have longitudinal-sensing axes 28 and 30 respectively. As shown in FIGS. 3–5, mercury switches 24 and 26 are positioned relative to a vertical axis 32. As shown in FIG. 3, both switches are open and thus not actuated. Assuming the sensor 10 is located on the right side of the human torso, FIG. 4 shows the effect of a person bending forward with a lumbosacral angle of alpha causing an actuation of switch 26 by allowing the mercury drop 27 to close contacts 29, $29^1$.

If the sensor 10 were located on the left side of a human body, and a person bent forward by an angle of alpha as shown in FIG. 5, switch 24 would be actuated. Thus, independent of which side the sensor 10 is placed, one of the two switches will actuate when the person bends forward past the critical angle.

Figure 6:
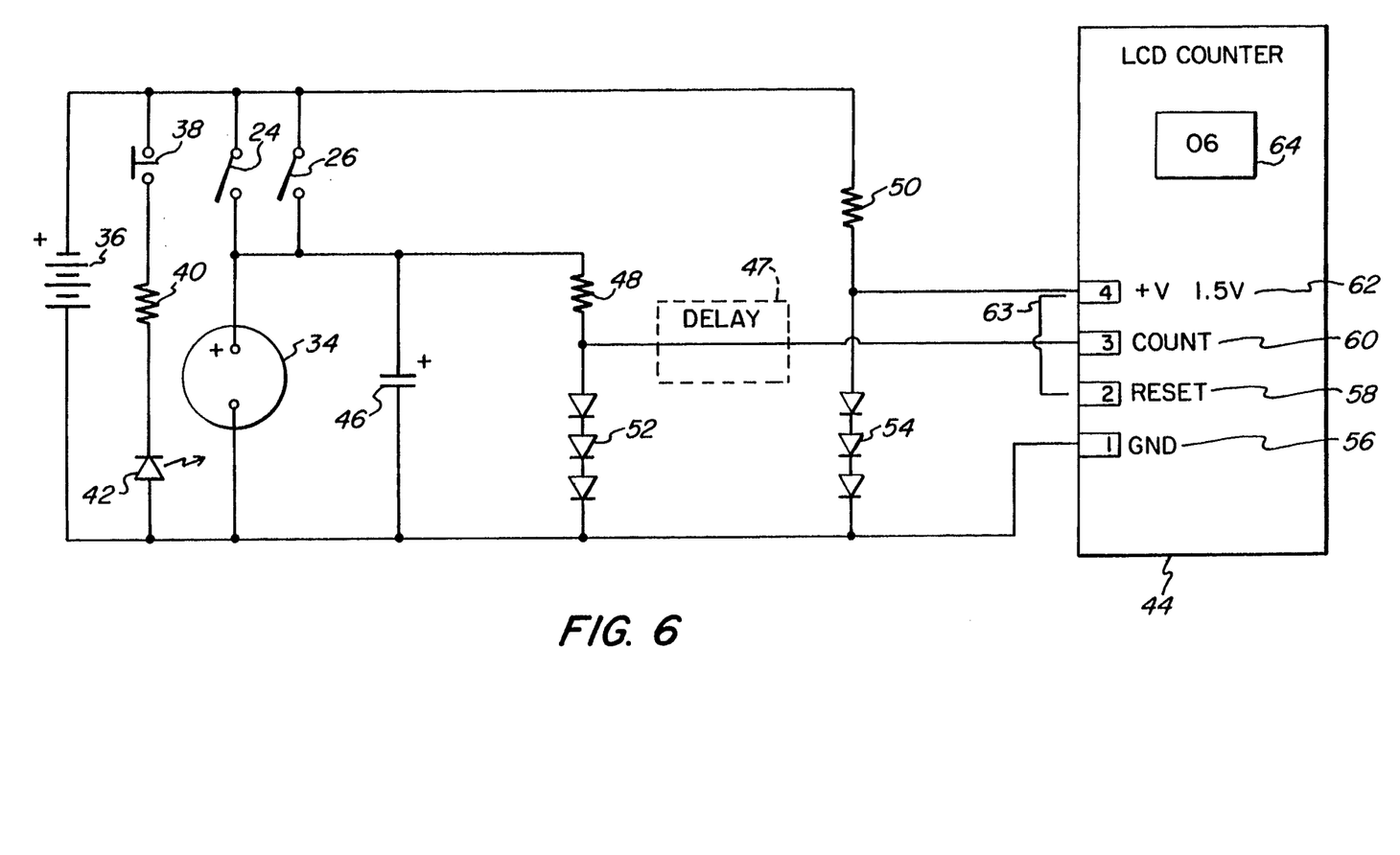
FIG. 6 is a schematic of the circuitry for the torso attitude sensor.

Referring to FIG. 6, the circuitry will now be described. The mercury switches 24 and 26 are connected in parallel to a buzzer 34 which sounds an audible alarm when one of the two switches is actuated. A power source such as a 12 volt battery 36 or equivalent is provided to power the buzzer 34. A battery test switch 38 is provided, and permits the person using the device to determine whether the battery has sufficient power to operate the buzzer. The test switch is connected through a resistor 40 and a light 42. A capacitor 46 is provided across buzzer 34 and filters transients from reaching or triggering a counter 44.

Further screening can be done by including a delay, such as shown in phantom at 47, by which the signal from an actuated switch 24 or 26 must persist for a minimum time in order to increment the count in counter 44. In such case if a person makes a quick jarring movement, a mercury switch may be momentarily actuated but a signal is not delivered to the counter. Only when a switch has been activated for a predetermined time will the count be incremented. Resistors 48 and 50 limit current flows. The group of diodes 52 and 54 limit input voltages to counter 44.

A counter chip 44 includes several ports including a ground 56, a reset 58, a count or input 60 and power input 62.

The counter chip 44 includes a digital readout 64 whose display indicates the number of actuations representative of excessive bending, in the illustrated counter a count of six.

In order to reset the counter, a connection must be made momentarily between the reset input 58 and the power input 62. This can either be done by a switch which is not shown, or preferably by a jumper wire 63 that is used to connect the reset contact 58 and the power voltage contact 62.

The readout 64 need not necessarily be visible from the exterior of the sensor 10. It may be desirable to have the counter not visible from the outside to keep the bending history of the person who is wearing the sensor private.

Figure 7:
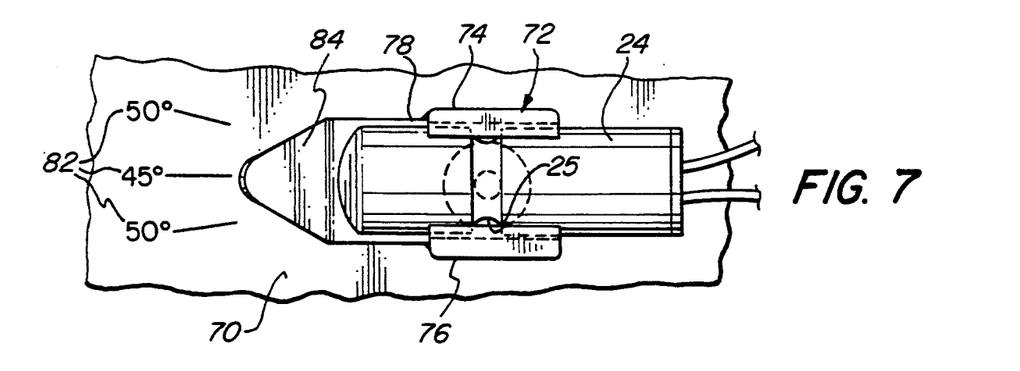
FIG. 7 is a top plan view of a mercury switch shown attached to a printed circuit board.
Figure 8:
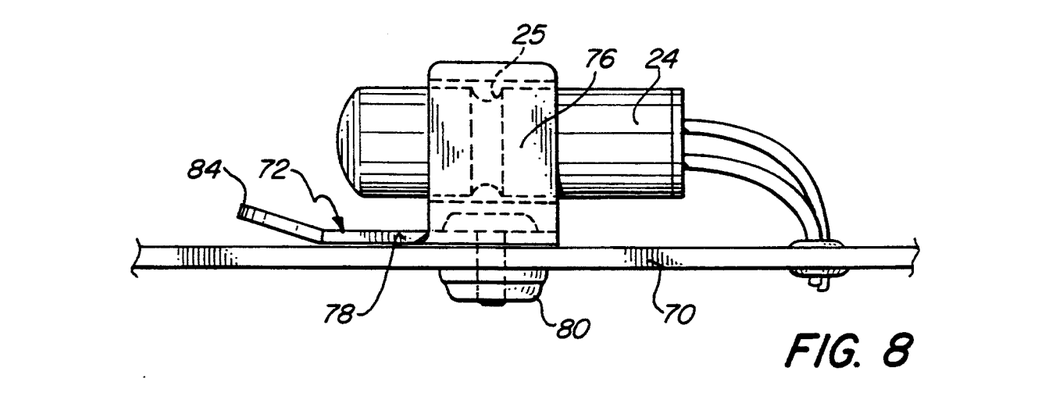
FIG. 8 is a side plan view of the switch shown in FIG. 7.

Referring to FIGS. 7 and 8, an adjustable mount for the mercury switch 24 or 26 is shown. The mercury switch 24 is mounted on a printed circuit board 70 by a metal mounting clip 72 that includes arms 74 and 76 that grasp the switch 24. The arms 74 and 76 extend outwardly from a base 78 that is attached to the printed circuit board 70 by a rivot 80. Angle notations 82 are printed or in some other manner placed on the printed circuit board 70 to indicate the angle of the switch 24 with respect to the vertical axis 32 (as shown in FIG. 3). The base 78 includes an integral pointer 84 that indicates the angle of the switch with respect to the vertical.

By using two mercury switches or other attitude responsive switches, the sensor can be placed on the left or the right side of the person who wears the sensor. The use of a filtering device such as delay 47 provides for counting only bona fide signals generated by the switches 24 and 26.

With respect to FIGS. 9–15, another back-bending sensing device 100 is shown. It has a housing 102 on the back of which a mounting clip 104 is located to clip onto a belt. Housing 102 has a window 110 through which a counter reading display 112 can be seen.

Housing 102 contains a printed circuit board 114 on which a pair of torso attitude-sensing switches 116, 118 are located with an orientation as shown for switches 24 and 26 in FIGS. 1–5. Switches 116, 118 need not have an internal ridge as described with reference to the embodiment shown in FIGS. 1–5. Board 114 carries an audible alarm transducer 120 of the type that requires a varying signal to activate it and is capable of generating a sufficiently loud warning to be heard in a typical noisy work environment. A battery 122 is located at the bottom of housing 102 to power the circuit.

Figure 12:
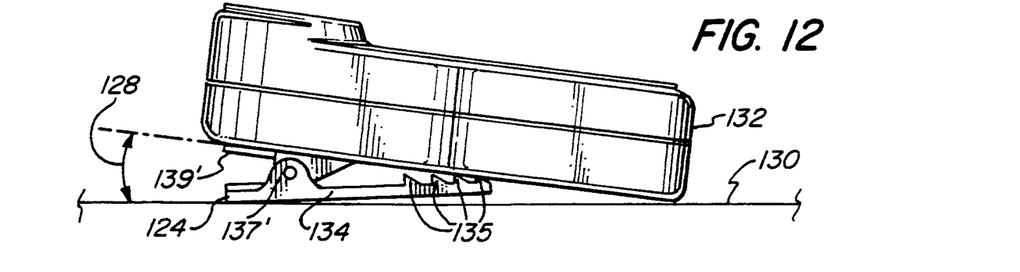
FIG. 12 is a side view in elevation of the back-bending sensing device when resting on a flat surface.
Figure 13:
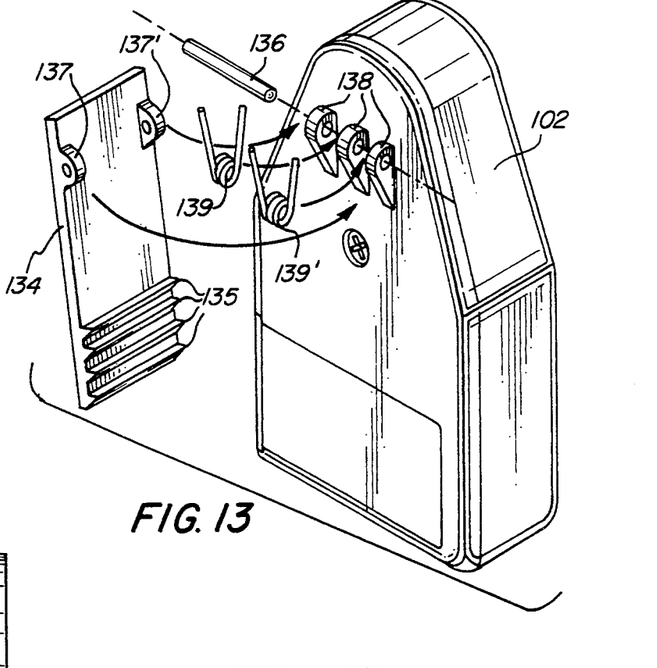
FIG. 13 is a perspective exploded view of the back-bending sensing device of FIG. 9 with the spring-clip mounting assembly shown disassembled.

Housing 102 and clip 104 conveniently form a stable resting place for device 100 as illustrated in FIG. 12. As shown, the belt clip 104 is so located that its upper straight edge 124 and the bottom corner edge 126 of housing 102 cause the housing to be inclined at an angle 128 relative to a flat surface 130. Angle 128 is sufficiently large so as to prevent the activation of the mercury torso attitude-sensing switches 116, 118 while in this position. Housing bottom 132 further preferably is flat to provide another stable placement position for device 100.

Figures 9, 10, 11:
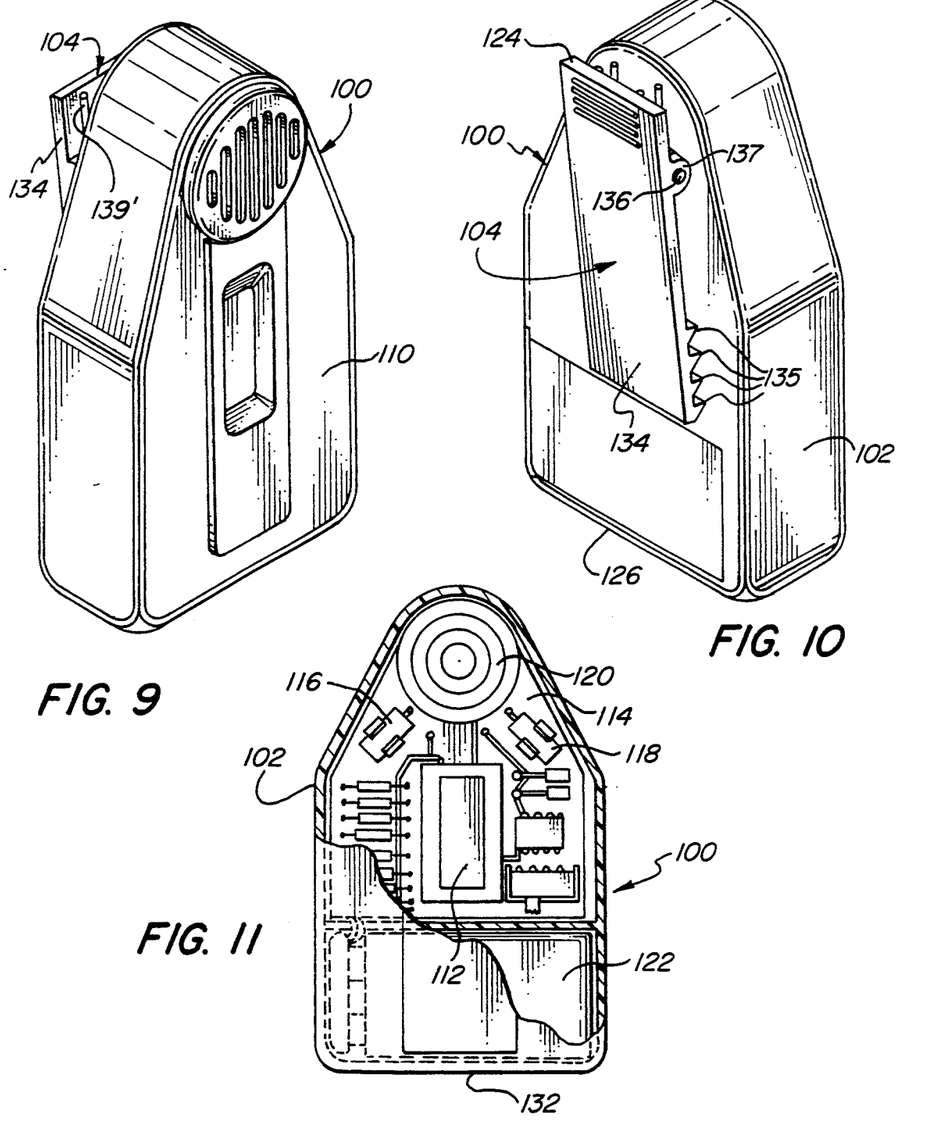
FIG. 9 is a perspective view of another back-bending sensing device.
FIG. 10 is a rear perspective view of the back-bending sensing device of FIG. 9.
FIG. 11 is a front elevation and partially cut-away view of the back-bending sensing device of FIG. 9.

The mounting clip 104 is formed with a spring-loaded lever 134 having a plurality of parallel aligned elongate teeth 135 at the lower end. A pivot pin 136 aligns lever-mounted hinge elements 137, 137' with corresponding hinge elements 138 on housing 102 and with springs 139, 139' so as to enable the lever 134 to be spring-loaded in the closed position as illustrated in FIGS. 10 and 12.

Figure 15:
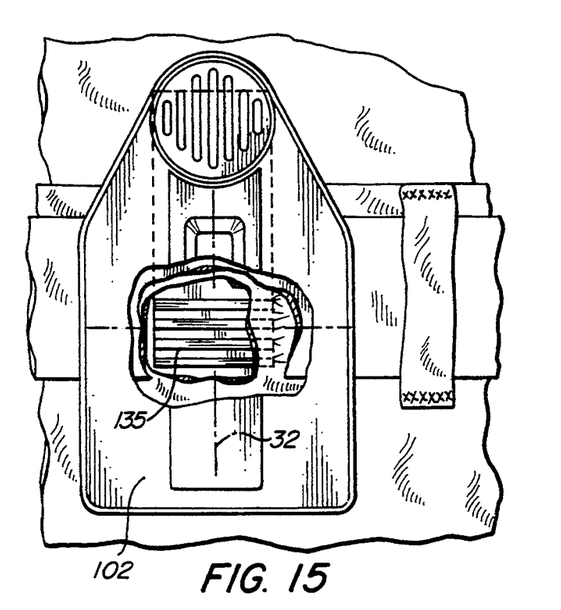
FIG. 15 is a rear, partially broken-away view of the device of FIG. 9.

The elongate teeth 135 can firmly grip into a part of a garment 141 and are so aligned with respect to the attitude sensing switches 116, 118 that these can be held in the desired orientation when the housing 102 is properly mounted to a belt as shown in FIG. 15.

Figure 14:
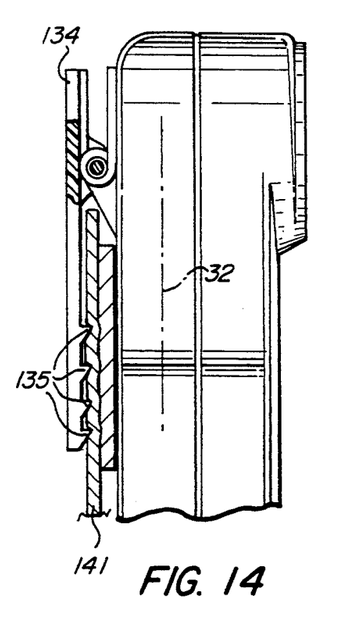
FIG. 14 is a partial side view of the back-bending sensing device when properly mounted.

As illustrated in FIGS. 14 and 15, the elongate teeth 135 are aligned substantially transversely to the local vertical axis 32. With teeth 135 digging into a fabric 141, housing 102 tends to remain in the desired orientation, thus assuring proper operation.

Teeth 135 are illustrated as elongate parallel rows. However, other arrangements can be used as long as the teeth cooperate with the garment to hold housing 102 in the proper alignment.

Figure 16:
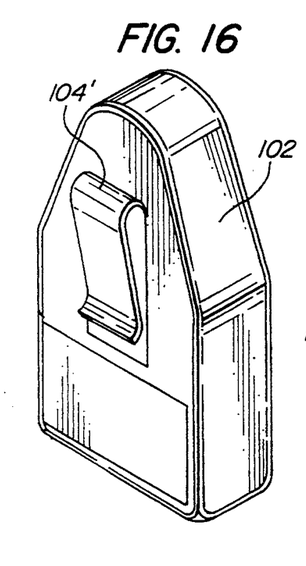
FIG. 16 is a rear perspective view of a back-bending sensing device as shown in FIG. 9, but with a different mounting clip.

FIG. 16 illustrates an alternate clip 104' that can be used to mount housing 102 to a belt.

Figures 17, 18, 19:
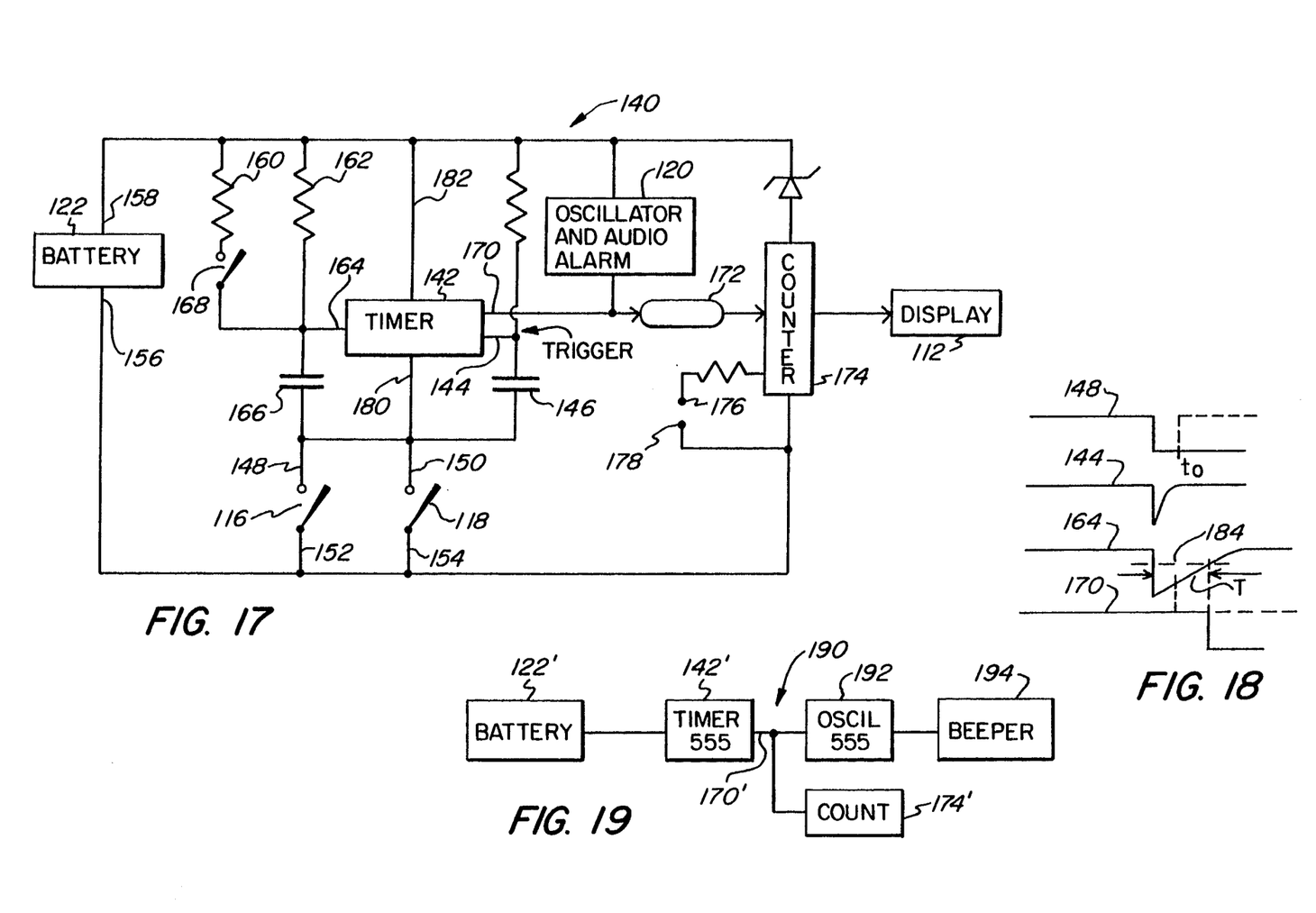
FIG. 17 is a schematic block diagram of a circuit used in the embodiment of FIG. 9.
FIG. 18 is a timing diagram for certain terminals in the circuit of FIG. 17.
FIG. 19 is a block diagram for a modified version of the circuit in FIG. 17.

With reference to FIG. 17, a circuit 140 is shown and is for use on printed circuit board 114. The circuit includes an audio alarm 120 which includes both an oscillator and audio transducer to generate an audible alarm. Such alarms are well known in the art. A timer 142 is connected in series with normally open back attitude-sensing switches 116, 118 and coupled across battery 122. Hence, no current is drawn by timer 142 as long as switches 116, 118 remain open.

Timer 142 is made by connecting a conventional 555 chip into a timer configuration as is well known in the art. In this configuration, a trigger input occurs on line 144 which is coupled by a capacitor 146 to the parallelly-connected terminals 148, 150 of switches 116, 118 respectively. The other terminals 152, 154 of the latter switches are connected to the return terminal 156 of battery 122. The high side, 158, of battery 122 is coupled to timer 142 and through a pair of parallel coupled resistors 160, 162 to a timing input 164. A capacitor 166 couples input 164 to terminals 148, 150. A manually-selectable switch 168 is placed in series with resistor 160 so that the interval that a switch 116 or 118 needs to be closed to produce a signal on output line 170 can be varied generally between about 150 (with switch 168 closed) to about 400 milliseconds (with switch 168 open) and preferably between 200 and 350 milliseconds.

The output line 170 is coupled through a coupling network 172 to a counter 174 similar to counter 44 in FIG. 6. A reset of counter 174 is obtained by interconnecting a pair of terminals 176, 178 which are located on board 114.

Operation of circuit 140 can best be understood with reference to FIG. 17 and the timing diagram of FIG. 18. Assume a person bends past the critical lumbosacral angle so that switch 116 is closed. This causes one side of both capacitors 146, 166 to be grounded and the positive potential on the other side, i.e., at terminals 144 and 164 to temporarily drop close to ground potential. With power now supplied to timer 142 along lines 180, 182, it is activated and begins to charge capacitor 166 through either resistor 162 or both resistors 162 and 160.

When the potential at terminal 164 reaches two-thirds of the battery potential as shown at 184, i.e., after an interval T, the output 170 changes and goes to ground. This, then provides energization of alarm 120 and increments counter 174 by one.

In the event switch 116 reopens before the interval T has passed, such as at time to in FIG. 18, power to timer 142 is interrupted, no change in the level of output line 170 occurs and no alarm is sounded from beeper 120.

FIG. 19 illustrates a modified network 190 for circuit 140. In network 190, a timer 142' functions as described for circuit 140. However, its output on line 170' drives an oscillator 192 formed by a 555 chip that is configured to provide a repetition rate of pulses at a frequency deemed desirable for an audio transducer 194, such as a tiny speaker. Various components shown in detail in FIG. 17 are included in the blocks of FIG. 19 such as battery 122' and a counter 174'.

It should be understood that although specific embodiments of the invention have been described herein in detail, such description is for purposes of illustration only and modifications may be made thereto by those skilled in the art within the scope of the invention.

We claim:

1. A torso attitude sensor for determining when a person bends the back at the waist past a predetermined lumbosacral angle, comprising:

a portable housing;

at least two attitude responsive switches secured inside the housing, one of said attitude responsive switches being so oriented as to be actuated when said portable housing is inclined in a first direction in excess of a predetermined lumbosacral angle relative to an upright affixation of the portable housing to a garment at the side of the waist;

another attitude responsive switch being so oriented as to be actuated when said housing is inclined by said predetermined lumbosacral angle in a second direction opposite to that of the first direction, means for mounting the housing to one of the left and right sides of a garment worn at the waist of the person to enable actuation of one of said switches when the housing is inclined past said predetermined lumbosacral angle when the person bends the back;

means for generating a signal when one of said attitude responsive switches is actuated by an inclination of the housing past said predetermined lumbosacral angle, means, mounted within the portable housing and effectively responsive to the signal, for accumulating a count of the number of times any one of said attitude responsive switches has been actuated as a result of said person having bent his or her back in excess of the predetermined lumbosacral angle and means, within the portable housing, for producing an output signal indicative of the accumulated count;

said means for accumulating a count having means for resetting the means for accumulating a count, said resetting means being located within said housing so as to reduce access to said resetting means by said person and enable reliable monitoring of bends by said person beyond said predetermined lumbosacral angle;

wherein said mounting means includes, means, affixed to a wall of the portable housing, for attaching the housing to one of the left and right sides of a garment worn at the waist of said person;

said attaching means including a plurality of elongate parallel teeth aligned substantially transverse to an upright alignment of the portable housing, said plurality of teeth cooperatively engaging said garment so as to maintain said upright affixation of the housing when worn by the person at the waist.

* * * * *